United States Patent [19]
Fukuda et al.

[11] Patent Number: 5,293,220
[45] Date of Patent: Mar. 8, 1994

[54] METHOD FOR INSPECTING STRIPPED CONDITION OF ELECTRIC WIRE

[75] Inventors: Michio Fukuda; Yoshihide Ichikawa, both of Mie, Japan

[73] Assignee: Sumitomo Wiring Systems, Ltd., Mie, Japan

[21] Appl. No.: 944,984

[22] Filed: Sep. 15, 1992

[51] Int. Cl.$^5$ .............................................. G01B 11/00
[52] U.S. Cl. ...................................... 356/394; 356/372; 382/8
[58] Field of Search .................. 356/372, 394, 237; 358/101, 106; 382/8

[56] References Cited

U.S. PATENT DOCUMENTS

4,649,621  3/1987  Dunsel et al. .

FOREIGN PATENT DOCUMENTS

| | | |
|---|---|---|
| 0031973 | 7/1981 | European Pat. Off. . |
| 2553914 | 10/1983 | France . |
| 57-198850 | 12/1982 | Japan . |
| 59-216044 | 12/1984 | Japan . |
| 60-174962 | 9/1985 | Japan . |

OTHER PUBLICATIONS

Patent Abstracts of Japan, vol. 10, No. 22, Group No. P424 60-174962, publication date Jan. 28, 1986.

*Primary Examiner*—F. L. Evans
*Attorney, Agent, or Firm*—Sughrue, Mion, Zinn, Macpeak & Seas

[57] ABSTRACT

A method for inspecting the stripped condition of an electric wire permits inspection of electric wires having a tip portion of various configuration with high accuracy and reliability. In this method, stripped condition is judged to be good or not good by: illuminating a core 6 at a tip portion of the electric wire 4 and its vicinity by means of illumination means 11; imaging the core and its vicinity by means of imaging means 12, the imaging means disposed in opposite relation to the illumination means 11 with the electric wire 4 therebetween; determining coordinate position of stripped end of the sheath in an imaging plane using illumination data of a picture obtained by the imaging means; determining coordinate position of the tip end of the core 6 in the imaging plane, as well as shape of the core 6, such as inclination of the core 6; determining as to whether the coordinate position of the stripped end is within a standard range, whether length and thickness of the core are within a standard range, or whether strands come out of the core.

2 Claims, 9 Drawing Sheets

W19

W19

W20

METHOD FOR INSPECTING STRIPPED CONDITION OF ELECTRIC WIRE

BACKGROUND OF THE INVENTION

1. Field of the Invention

This invention relates to a method for inspecting the stripped condition of electric wires.

2. Statement of the Prior Art

Conventionally, it is known that the stripped condition of a tip of electric wire, for use in wiring harnesses or the like, is inspected by means of a conductibility inspection method. For convenience of illustration, such a method will be explained below with reference to FIGS. 13, 14 and 15. FIG. 13 is a schematic circuit diagram for a prior art conductibility inspection method. FIG. 14 is a view illustrating operation of the conductibility inspection method. FIG. 15 is a view illustrating various stripped conditions of electric wires.

As shown in FIG. 13, a prior art conductibility inspection circuit includes a battery 1, a resistor 2 and a light emitting diode 3, all connected in series. The conductibility inspection circuit is connected at one end thereof to a conductor of an electric wire 4, and connected at the other end to a contact 5. The contact 5 is contacted with a core 6 of the electric wire 4 which has been stripped of its cover so as to check if the light emitting diode 3 will be lighted due to the electric current through to the light emitting diode 3 in the conductibility inspection circuit. When the tip portion of the electric wire 4 has been stripped of its cover to some extent, the core 6 and contact 6 are securely contacted with each other, so that the light emitting diode 3 will be lighted.

Thus, it is determined that the stripped condition of an electric wire is "good" when the light emitting diode 3 is lighted. On the other hand, if the light emitting diode 3 is not lighted, it is determined that the stripped condition of the electric wire is "not good" or "poor".

Another method for inspecting the stripped condition of electric wire is shown in FIG. 14. According to this method, a box 7 housing therein a light source and an additional box 8 in opposed relation to the box 7 are provided. The box 7 is formed with two slits 9a and 9b. The box 8 includes light receiving elements at positions opposite to the slits 9a and 9b, respectively. Electric wire 4 is moved at a constant speed between the boxes 7 and 8 in a manner such that a core 6 of the wire will block a beam of light from one slit 9a, while the sheath of the wire will block a beam of light from the other slit 9b. A cross-sectional area of the core 6 having been stripped off can be calculated using the variations in waveform of output signals from the light receiving elements, so that the stripped condition of the wire may be determined.

With the above method, it is merely determined whether or not the tip portion of the wire 4 is stripped of its sheath so as to expose its core. It is, however, not possible to determine the shape or configuration of the core 6, i.e., length or thickness of the core exposed or stripped off.

Another method for inspecting stripped condition of electric wire is also known, which utilize a picture processing technique. For example, Japanese Patent Public Disclosure No. 57-198850 discloses a method for inspecting looseness of sheath material and deviation of stripped position by a binary processing of a picture obtained from a one-dimensional image sensor. Japanese Patent Public Disclosure No. 59-216044 also discloses an inspection method in which collimated light is illuminated onto a tip portion of a wire which is clamped, the shade behind the wire is received by a one-dimensional light receiving means oriented perpendicularly to the wire, and moving the light receiving means along the length of the wire so as to determine the good or not good condition of the wire end on the basis of light information received by the light receiving means.

It is noted, however, that, actually, a tip portion of a stripped wire 4 may take a various configuration as shown in FIG. 15. For example, the tip portion may have strands coming out, dispersion, or expansion of a core (a, b and c, respectively), defects in sheath (d), deformation of a core (e) and the like. These shapes may cause a problem during installation of a crimp-style terminal thereon, so that such wires should be determined to be in a not good stripped condition. The above method utilizing conventional picture processing technique is incapable of detecting such detailed configuration of the tip portion of wires as mentioned above, so that they are disadvantageous in carrying out inspection with high accuracy and reliability.

SUMMARY OF THE INVENTION

A primary object of the invention is to provide a method for inspecting the stripped condition of electric wires having various tip configurations with high accuracy and reliability on the basis of judging the coordinate position of the stripped end, length and thickness of a core, or of a strand out of the core, so as to determine if the stripped condition is good or not good.

Present invention provides a method for inspecting stripped wire to determine if the wire is in good or not good stripped condition, the wire having been stripped of a length of sheath by means of a stripper for installation of a crimp-style terminal thereon. The method comprises the steps of: illuminating a core at a tip portion of said wire and its vicinity by means of illumination means, the tip portion being exposed due to stripping; imaging the core and its vicinity by means of imaging means, the imaging means disposed in opposite relation to the illumination means with the electric wire therebetween; determining coordinate position of stripped end of the sheath in an imaging plane of the imaging means using illumination data of a picture obtained by the imaging means; determining the coordinate position of the tip end of the core in the imaging plane, as well as the shape of the core, such as an inclination of the core; and determining whether the coordinate position of the stripped end is within a standard range, whether the length and thickness of the core are within a standard range, or whether strands come out of the core.

According to the invention, inspection of stripped wires having various tip configurations can be carried out with high accuracy and reliability, since good or not good condition is judged by: illuminating a core at the tip portion of the wire and vicinity of the core by means of illumination means; imaging the core and its vicinity by means of imaging means which is disposed in opposite relation to the illumination means with the wire disposed therebetween; obtaining a clear variable-density picture having a dark portion at which light is blocked by the tip portion of the wire and remaining bright portion; determining from illuminance data of the picture coordinate position of a stripped end of a sheath in an imaging plane, coordinate position of the tip of the core in the imaging plane, and configuration of the core, such as inclination of the core; determining as to whether the coordinate position of the stripped end is within a standard range, whether the length and thickness of the core are within a standard range, or whether strand out of the core exists.

BRIEF DESCRIPTION OF THE DRAWINGS

For a better understanding of the invention, and to show how the same may be carried out into effect, reference will now be made, by way of example, to the accompanying drawings in which like reference numeral refer to like elements.

DETAILED DESCRIPTION OF THE PREFERRED EMBODIMENTS

Several embodiments of a method for inspecting the stripped condition of electric wire according to the invention will be explained below with reference to FIGS. 1 to 12.

Figure 1:
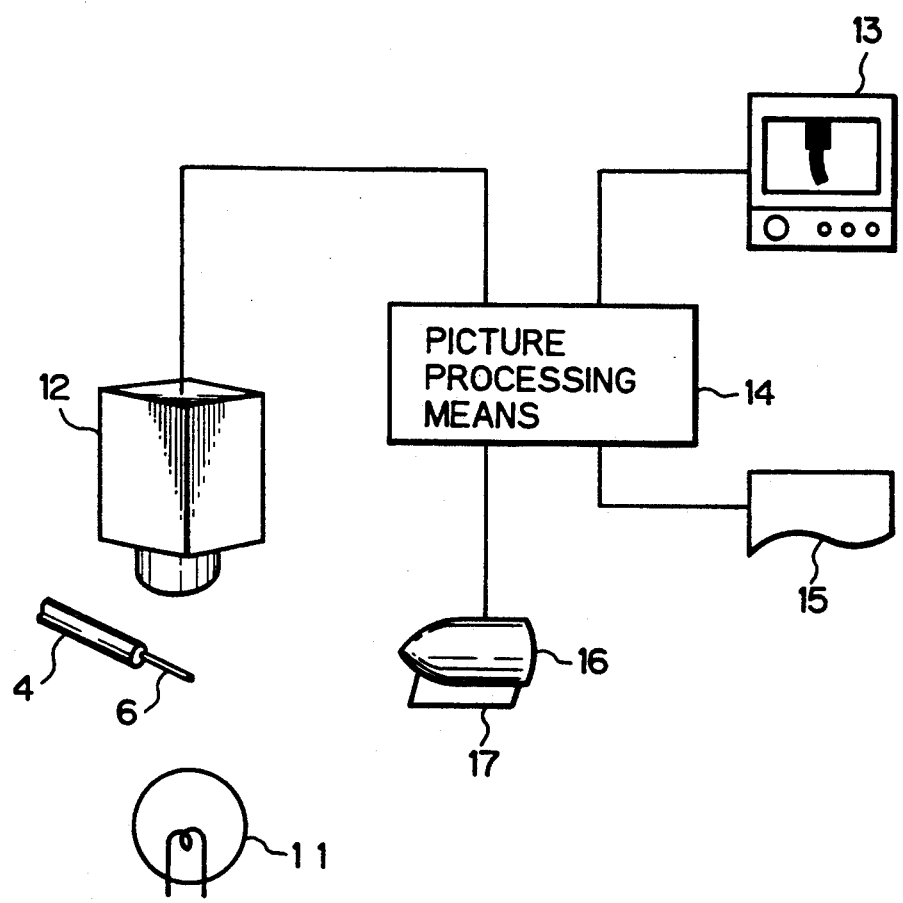
FIG. 1 is a schematic view of an inspection device for use with a method for inspecting stripped condition of electric wire according to one embodiment of the invention.

FIG. 1 shows one embodiment of a method for inspecting the stripped condition of electric wire according to the invention, together with general construction of an inspection device for use in the inspection method.

First, the inspection device will be described. As shown in FiG. 1, illumination means 11 illuminates electric wire 4 at and around the tip portion of a core 6 which has been stripped of sheath material or cover. The core 6 and its vicinity are imaged by imaging means 12, such as a television camera, two-dimensional CCD camera or the like, disposed opposite to the illumination means 11 with the electric wire 4 therebetween. A picture obtained by the imaging means 12 is displayed on a monitoring television receiver 13 (hereinafter, simply referred to as a monitor) and the picture is processed by picture processing means 14. From each luminance data of pixel, a coordinate position of the imaging means 12 in a imaging plane at a stripped end is conducted, as well as a coordinate position of the tip of the core 6 in the imaging plane, and the shape of the core 6 such as an inclination of the core 6.

The picture processing means 14 determines if the coordinate position of the stripped end as conducted is within a prescribed or standard range, if the thickness and length of the core are in their respective prescribed or standard range, and if strands come out of the core 6. Thus, it is determined if the wire 4 is in "good" or "no good" stripped condition, and the result will be indicated by means of a printer 15 or a display 16.

Reference numeral 17 denotes an operational keyboard for inputting program data necessary for picture processing.

Picture processing to be carried out by the picture processing means 14 will be explained with reference to FIG. 2. This process basically relies upon a method called "run-length coding", whereby the shape of an object (i.e. wire 4) and the like will be obtained on the basis of variation of white and black information along a single scanning line.

Figure 2:
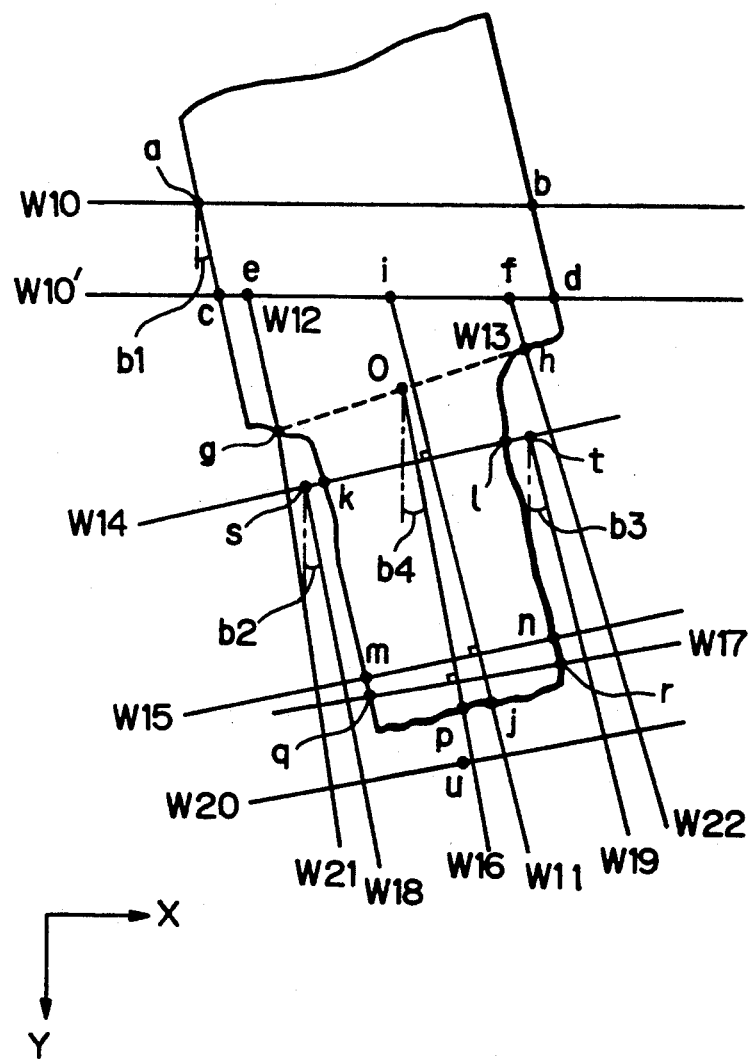
FIG. 2 is an illustrative diagram of operation of FIG. 1.
Figure 3:
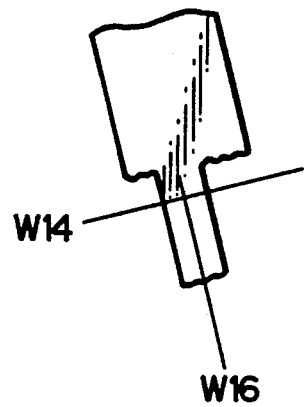
FIG. 3 is an illustrative view of operation of FIG. 1.

As shown in FIG. 2, reference lines W10 and W10' are set at predetermined coordinate positions so that they extend over the tip portion of the wire 4. From luminance data of each of the pixels on the reference lines W10 and W10', intersections a, b, c and d between the reference lines W10 and W10' and the boundary lines of the wire 4 are obtained.

In this regard, it is to be noted that, since the wire 4 is illuminated by the imaging means 12 from its backside, the illumination light is blocked by the wire 4, so that a picture will have a black portion corresponding to the wire 4 and a white portion corresponding to the periphery around the wire.

Points e and f will be set at positions distant from points c and d by a predetermined number of pixels a1 in +X and −X directions, respectively. Stripped end detection windows or lines W12 and W13 are defined. These lines are started from points e and f, respectively, and have an inclination of b1 which is equal to that of the segment a-c. Points g and h corresponding to the stripped end are defined. A window 11 started from the intermediate point i between points c and d and having inclination b1 is defined. Thus, point j corresponding to a provisional tip end of the core 6 is defined.

In this regard, it should be noted that windows W11, W12 and W13 are in parallel relative one another.

Then, window W14 is defined. The window W14 passes through a point distant from point g shown in FIG. 2 by a predetermined number of pixels a2 and a3 in the X and Y directions, respectively, and is perpendicular to a line extended from segment a-c. Window W15 is defined which passes through a point distant from point j by predetermined numbers of pixels a4 and a5, respectively, and which is perpendicular to segment a-c. From the luminance data of each of the pixels on the windows W14 and W15, the intersections k, l, m and n between the windows W14 and W15 and the boundary lines of the core 6. The inclinations b2 and b3 of segments k-l and m-n are defined as the inclinations at the left-hand side and right-hand side, respectively, of the core 6.

Window W16 is drawn from the intermediate point of segment g-h with an inclination b4 which is a mean value of b2 and b3 as defined above. Point p corresponding to the true tip of the core 6 is defined. Then, window W17 is defined, which passes through a point distant from point p by a predetermined number of pixels a6 and a7 in the X and Y directions, respectively, and which is perpendicular to window 16 having inclination b4. Then, intersections q and r between the window W17 and the boundary lines of the core 6 are defined. Thus, width at the tip of the core 6 (core width) is defined as the length of segment q-r.

Window W18 is defined as starting, from a points s on window W14 distant from point k by a predetermined number of pixels a8 and a9 in the X and Y directions, respectively, and which has an inclination b2. Similarly, window W19 is defined as starting, from point t on window W14 distant from point 1 by a predetermined number of pixels a10 and a11 in the X and Y directions, respectively, and which has an inclination b3. These windows will be used as reference lines for detection of "strand out" of the core 6. Window 20 is defined, which passes through a point u distant from point p by predetermined numbers of pixels a12 and a13 in the X and Y directions, respectively, and which is perpendicular to the window 16 having inclination b4. This window is specifically used as a reference line for detection of strand out of the core 6 at the tip thereof. Then, windows W21 and W22 are defined which are started from point g and h, respectively, and have inclination b2 and b3, respectively. These windows are also used as reference lines for detection of strand out of the core 6.

Figure 4A:
FIGS. 4(a) and 4(b) are illustrative views of operations of FIG. 1.
Figure 4B:
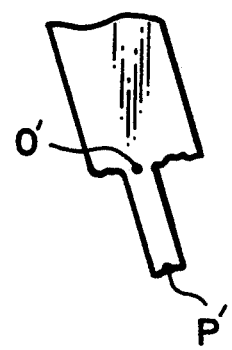

Detection of stripped length and stripped thickness in order to determine as to whether they are in "good" or "not good" condition will be carried out on the basis of windows W16 and W14, respectively. Improper chuck position is detected on the basis of the coordinate position of point o and p. FIG. 4a illustrates proper or good chuck position, while FIG. 4b illustrates improper or not good chuck position as indicated by points o' and p'.

Figure 5:
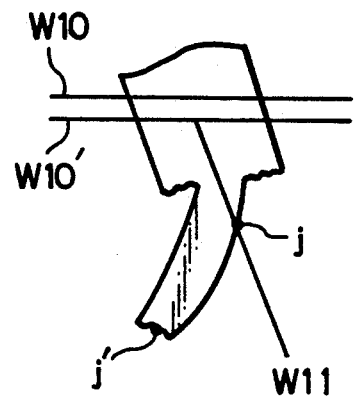
FIG. 5 is an illustrative view of operation of FIG. 1.
Figure 6:
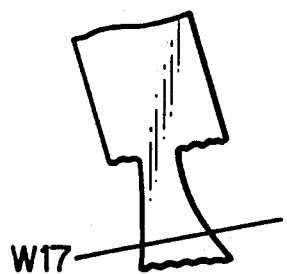
FIG. 6 is an illustrative view of operation of FIG. 1.

When the core portion and sheath portion are deformed at a different angle or inclination, as shown in FIG. 5, point j will be determined as tip end position of the core on the basis of window 11. It will be appreciated, however, that the actual tip end of the core is located at point j'. Thus, improper deformation will be detected on the basis of a difference between points j and j'. Improper expansion of the core will be detected on the basis of window W17 as shown in FIG. 6.

Figure 7:
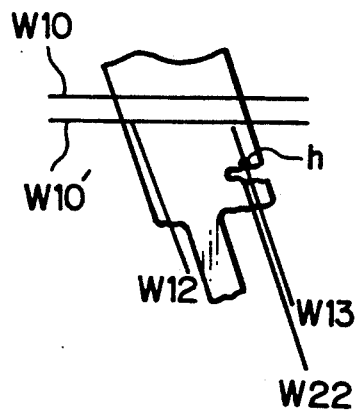
FIG. 7 is an illustrative view of operation of FIG. 1.
Figure 8:
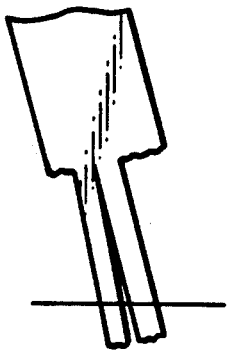
FIG. 8 is an illustrative view of operation of FIG. 1.

Improper defect of the sheath will be detected on the basis of window W22 starting from point h detected by window W12 as a stripped end, as shown in FIG. 7. Improper dispersion of the core will be detected as insufficient core thickness on the basis of window W17, as shown in FIG. 8.

Figure 9A:
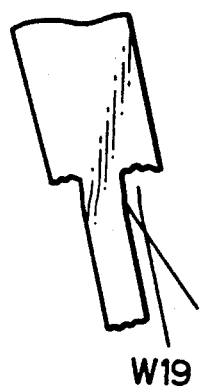
FIGS. 9(a) and 9(b) are illustrative views of operations of FIG. 1.
Figure 9B:
Figure 10:
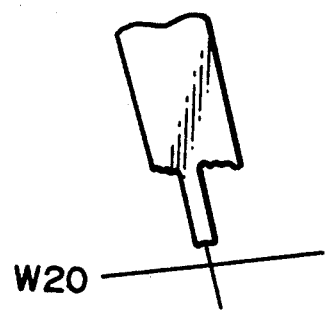
FIG. 10 is an illustrative view of operation of FIG. 1.

Improper strands coming out of the core will be detected on the basis of window W19, as shown in FIG. 9a. Even when significant strands coming out occurs as shown in FIG. 9b, it may be detected on the basis of window W19. A portion having a thickness larger than the core thickness will be determined as a main core. Improper strands coming out from the core tip will be detected on the basis of window 20, as shown in FIG. 10.

A sequential operation for detection of the stripped condition of wire will be explained below with reference to the flow chart shown in FIG. 11.

Figure 11:
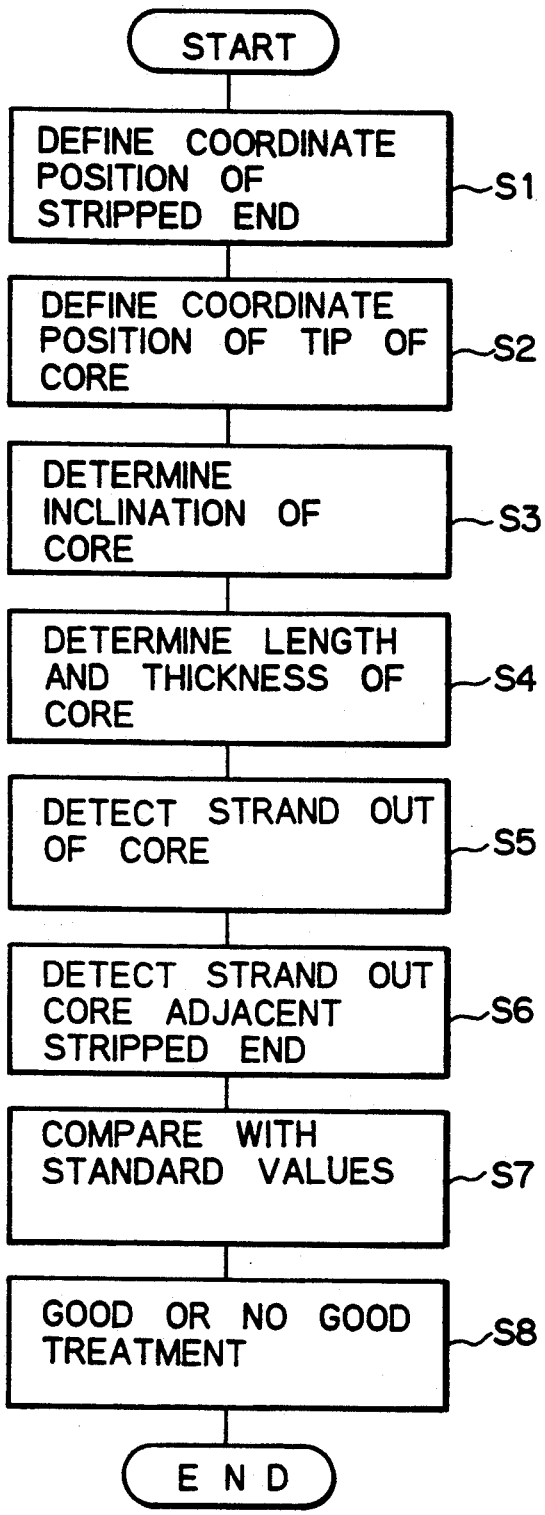
FIG. 11 is a flow chart illustrating operation of FIG. 1.

Pictures obtained by the imaging means 12 are processed in the above manner as shown in FIG. 11. Coordinate positions g and h in FIG. 2 are defined so as to determine coordinate position of the stripped end of the wire 4 (step S1). Coordinate position of point p in FIG. 2 is defined so as to determine the tip end of the core 6 (step S2). Inclination b4 of window 16 is defined so as to determine the inclination of the core 6 (step S3).

Length of segment o-p in FIG. 2 is defined so as to determine the length of the core 6. Length of segment q-r connecting points q and r is defined so as to determine the thickness of the core 6 (step S4). Presence of any strands coming out around and tip of the core 6, together with dispersion and expansion of the core, is detected on the basis of windows W18, W19 and W20 (step S5). Presence of any strand out in the vicinity of the stripped end of the core 6 is detected on the basis of windows W21 and W22 (step S6).

Then, the coordinate position of points g and h are compared with upper and lower limit of a standard range. It is determined if the coordinate position of the stripped end is within the standard range. It is also determined if the length and thickness of the core 6 are within their respective standard range by comparing them with upper and lower limit of the standard range. Further, presence of strands coming out, dispersion or expansion of the core 6 is determined (step S7). When the coordinate position of the stripped end is within the standard range, the length and thickness of the core 6 are within their respective standard ranges, no strand out of the core 6 is detected, and all standard for striped condition is cleared, the stripped condition of the wire 4 will be determined to be "proper" or "good". When any one of the above standard is not cleared, the tip portion of the wire 4 will cause something problematic during connection of a crimp-style terminal thereon, so that such wire is determined in "improper" or "not good" condition. Appropriate treatment will be done depending upon good or not good result (step S8). When a wire is determined to be in not good stripped condition, an alarm signal will be generated so as to inform an operator to that effect, whereby he may remove such an improper wire.

FIG. 2 illustrates an ordinary wire 4 in which the core 6 has been exposed over a relatively short distance for use with a crimp-style terminal. Since joint wires have a core exposed over a relatively long distance, picture processing procedure is slightly different from that of the ordinary wire. Such a picture processing procedure will be briefly explained below.

Figure 12:
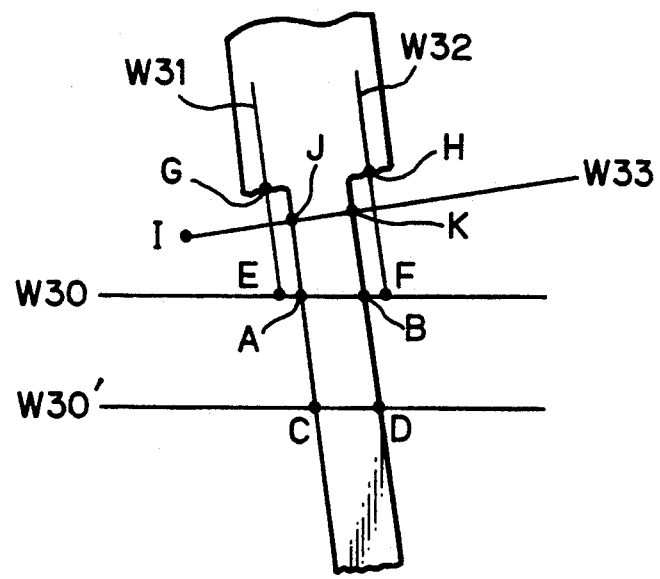
FIG. 12 is an illustrative view of operation of FIG. 1.
Figure 12:
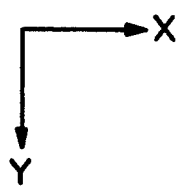
Figure 13:
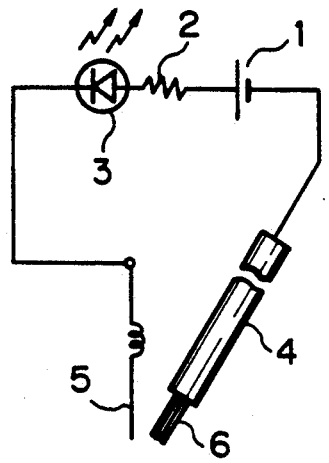
FIG. 13 is an illustrative view of operation of prior art method for inspecting stripped condition of electric wire.
Figure 14:
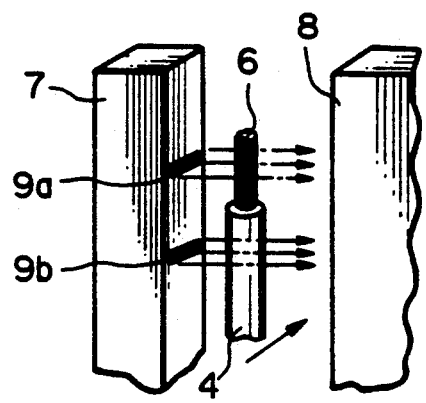
FIG. 14 is an illustrative view of operation of prior art method for inspecting stripped condition of electric wire.
Figure 15:
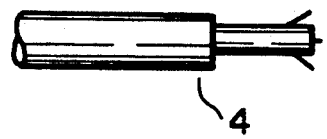
FIGS. 15(a)-15(e) illustrate various stripped conditions of electric wire.
Figure 15:
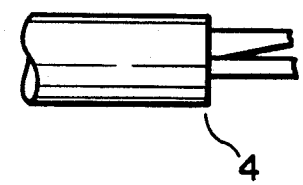
Figure 15:
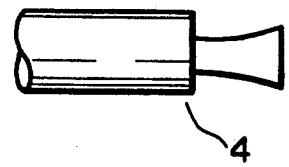
Figure 15:
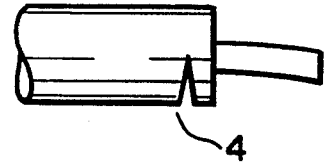
Figure 15:
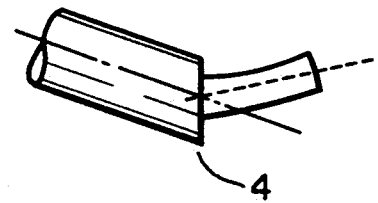

As shown in FIG. 12, windows W30 and W30' are drawn so that they extend across a picture of the core 6. Intersections A, B, C and D between the reference lines W30 and W30' and the boundary lines of the core 6 are defined. Inclination of the core 6 is determined to be a mean value b3 of the inclinations b1 of segment A-C and b2 of segment B-D.

Point E distant from point A by a predetermined number of pixels in the direction of −X, and point F distant from point B by the same number of pixels in the direction of +X are defined. Windows W31 and W32 starting from points E and F, respectively, and having an inclination b3 are defined. Intersections G and H between windows W31 and W32 and boundary lines representing the stripped end surface of the sheath are defined. The coordinate positions of the intersections G and H are regarded as coordinate positions of the stripped end.

Inclination b4 of the segment G-H is defined. Window W33 starting from point I distant from point G by a predetermined number of pixels in each of the directions of −X and +Y and having inclination b4 is defined. Intersections J and K between window W33 and the boundary line of the core 6 are defined. Length of segment J-K is regarded as a thickness of the core 6.

A series of operation for inspecting stripped condition of the wire is the same as that for the above ordinary wire.

From luminance data of pixels at the tip portion of the wire 4 obtained by the imaging means 12, coordinate position of the stripped end of the sheath in the imaging plane, and shape of the core 6, such as inclination of the core 6, are conducted. Stripped condition of the wire is judged to be good or not good, depending upon the fact that if the coordinate position of the stripped end is within a standard range, if the length and thickness are within their respective standard range, and if there is any strand coming out of the core 6. Inspection for stripped condition of wires having a tip portion of various configuration may be carried out with great accuracy and reliability. Judgment is automatically made with high accuracy as to whether a particular stripped condition is suitable for installation of a crimp-style terminal.

In accordance with another embodiment of the invention, additional imaging means is provided. It is possible to take image of the core 6 and its vicinity perpendicularly to both the imaging direction of the imaging means 12 and axial direction of the wire 4 in FIG. 1, thus reducing the possibility of "blind spot" when using a single imaging means 12. This increases accuracy and reliability of the inspection since the additional imaging means makes it possible to detect or determine elliptical or oval deformation of the core 6, strands coming out of the core in the imaging direction, and break or cut off of the core, which cannot be detected by means of a single imaging means.

The construction of the inspection device is not necessarily limited to the above embodiments. Detailed process of the picture processing is not limited to that shown in FIG. 2. Further, stripped condition may be determined on the basis of other factors, other than coordinate position of the stripped end, length and thickness of the core, and strands coming out of the core.

In accordance with the method for inspecting the stripped condition of electric wires, stripped condition is judged to be good or not good on the basis of whether or not coordinate position of the stripped end is within a standard range, whether or not the length and thickness of the core is within their respective standard ranges, or whether or not strands coming out of the core. Thus, it is possible to conduct an inspection with high accuracy and reliability with respect to electric wires having tip portion of various configuration. Adaptability of a particular stripped end of a wire may be accurately determined. The method provides a quite effective means for monitoring stripped wires in an automated line.

What is claimed is:

1. A method of inspecting a stripped wire to determine if the wire is in good or poor stripped condition, said wire having been stripped of a length of sheath to form a stripped end by means of a stripper for installation of a crimp-style terminal thereon, said method comprising the steps of:
    illuminating a core at a tip portion of said wire and its vicinity by means of illumination means, said tip portion being exposed due to stripping;
    imaging said core and its vicinity by an imaging means, said imaging means disposed in opposite relation to said illumination means with said wire therebetween;
    determining a coordinate position of said stripped end of said sheath in an imaging plane of said imaging means using illumination data of a picture obtained by said imaging means;
    determining a coordinate position of a tip end of said tip portion of said wire in said imaging plane;
    determining a shape of said core; and
    determining at least one of whether said coordinate position of said stripped end is within a standard range, whether a length and a thickness of said core are within a standard range, and whether there are strands coming out of said core.

2. The method as claimed in claim 1, wherein said step of determining the shape of said core further comprises determining the inclination of said core.

* * * * *

UNITED STATES PATENT AND TRADEMARK OFFICE
CERTIFICATE OF CORRECTION

PATENT NO. : 5,293,220
DATED : March 8, 1994
INVENTOR(S) : Michio Fukuda, et. al.

It is certified that error appears in the above-indentified patent and that said Letters Patent is hereby corrected as shown below:

On the Title page, item [30], Foreign Application Priority Data, insert--
Sept. 19, 1991   [JP]   Japan            3-268771--.

Signed and Sealed this

Thirtieth Day of August, 1994

Attest:

BRUCE LEHMAN

Attesting Officer          Commissioner of Patents and Trademarks